(12) United States Patent
Morio et al.

(10) Patent No.: US 10,386,307 B2
(45) Date of Patent: Aug. 20, 2019

(54) METHOD OF CREATING QUALITY GRADE DISCRIMINATION CRITERIA IN GRANULAR MATERIAL APPEARANCE QUALITY GRADE DISCRIMINATION DEVICE

(71) Applicant: Satake Corporation, Tokyo (JP)

(72) Inventors: Yoshinari Morio, Tsu (JP); Hiroki Ishizuki, Hiroshima (JP); Hideaki Ishizu, Hiroshima (JP); Hiroaki Takeuchi, Hiroshima (JP); Tatsuhiko Ochi, Hiroshima (JP)

(73) Assignee: SATAKE CORPORATION, Tokyo (JP)

( * ) Notice: Subject to any disclaimer, the term of this patent is extended or adjusted under 35 U.S.C. 154(b) by 22 days.

(21) Appl. No.: 15/315,427

(22) PCT Filed: Jun. 2, 2015

(86) PCT No.: PCT/JP2015/065922
§ 371 (c)(1),
(2) Date: Dec. 1, 2016

(87) PCT Pub. No.: WO2015/186708
PCT Pub. Date: Dec. 10, 2015

(65) Prior Publication Data
US 2017/0199132 A1 Jul. 13, 2017

(30) Foreign Application Priority Data

Jun. 5, 2014 (JP) .................................. 2014-117106

(51) Int. Cl.
*H04N 9/47* (2006.01)
*G01N 21/85* (2006.01)
(Continued)

(52) U.S. Cl.
CPC .............. *G01N 21/85* (2013.01); *G01B 11/02* (2013.01); *G01B 11/24* (2013.01); *G01B 11/28* (2013.01);
(Continued)

(58) Field of Classification Search
CPC ................. G06T 7/0004; G06T 11/001; G06T 2207/10024; G06T 2207/30128; G01B 11/2518
(Continued)

(56) References Cited

U.S. PATENT DOCUMENTS 4,884,696 A * 12/1989 Peleg ........................ B07C 5/00
209/545
2011/0194159 A1 8/2011 Hara et al.
(Continued)

FOREIGN PATENT DOCUMENTS

JP 2000146847 A 5/2000
JP 2002312762 A 10/2002
(Continued)

OTHER PUBLICATIONS

International Search Report for Application No. PCT/JP2015/065922 dated Aug. 25, 2015.

*Primary Examiner* — Jamie J Atala
*Assistant Examiner* — Masum Billah
(74) *Attorney, Agent, or Firm* — Joseph P. Farrar, Esq.

(57) ABSTRACT

A method of creating quality grade discrimination criteria in a discrimination device that determines appearance quality grades of granular materials in accordance with the present invention includes a granular material placement step of sorting the granular materials on a per-quality-grade basis and placing the granular materials on an image-capture surface of the image-capturing unit; an imaging data acquisition step of capturing images of the granular materials
(Continued)

placed on the image-capture surface by the image-capturing unit and thereby obtaining imaging data; a quality grade information acquisition step of obtaining, on a per-quality-grade basis, pieces of quality grade information on the respective granular materials on the basis of the imaging data; and a quality grade discrimination criteria creation step of creating quality grade discrimination criteria by using the quality grade information obtained on a per-quality-grade basis.

6 Claims, 6 Drawing Sheets

(51) Int. Cl.
    *G01B 11/28*     (2006.01)
    *G01B 11/02*     (2006.01)
    *G01B 11/24*     (2006.01)
    *G01N 21/88*     (2006.01)
    *G06T 7/60*     (2017.01)
    *G06K 9/00*     (2006.01)
    *G06K 9/03*     (2006.01)
    *G06K 9/62*     (2006.01)
    *G06T 7/00*     (2017.01)

(52) U.S. Cl.
    CPC ......... *G01N 21/88* (2013.01); *G06K 9/00147* (2013.01); *G06K 9/036* (2013.01); *G06K 9/6257* (2013.01); *G06T 7/0004* (2013.01); *G06T 7/60* (2013.01); *G01N 2021/8592* (2013.01); *G01N 2201/12* (2013.01); *G06T 2207/20081* (2013.01); *G06T 2207/30128* (2013.01)

(58) Field of Classification Search
    USPC .......................................................... 348/92
    See application file for complete search history.

(56) References Cited

U.S. PATENT DOCUMENTS

| | | | |
|---|---|---|---|
| 2013/0051622 A1* | 2/2013 | Ishizuki | ................ G01N 21/84 382/103 |
| 2014/0147015 A1* | 5/2014 | Bajema | ................ G06T 7/0004 382/110 |
| 2015/0076042 A1 | 3/2015 | Miyamoto et al. | |
| 2015/0146938 A1 | 5/2015 | Matsushima et al. | |

FOREIGN PATENT DOCUMENTS

| | | |
|---|---|---|
| JP | 2010060389 A | 3/2010 |
| JP | 2011242284 A | 12/2011 |
| JP | 2013033331 A | 2/2013 |
| WO | 2010041388 A1 | 4/2010 |
| WO | 2013145873 A1 | 10/2013 |
| WO | 2014002636 A1 | 1/2014 |

* cited by examiner

METHOD OF CREATING QUALITY GRADE DISCRIMINATION CRITERIA IN GRANULAR MATERIAL APPEARANCE QUALITY GRADE DISCRIMINATION DEVICE

CROSS-REFERENCE TO RELATED APPLICATIONS

The present application is a national phase entry under 35 U.S.C. § 371 of International Application No. PCT/JP2015/065922, filed Jun. 2, 2015, which claims priority from Japanese Application No. 2014-117106, filed Jun. 5, 2014, the disclosures of which are incorporated by reference herein.

TECHNICAL FIELD

The present invention relates to a method of creating criteria for determining quality grades of granular materials such as grains and pellets in a discrimination device that determines appearance quality grades of granular materials.

BACKGROUND ART

A discrimination device that determines appearance quality grades of grains is known, which captures images of grains by an image-capturing unit such as a scanner and obtains imaging data, and determines quality grades of the grains based on the imaging data (for example, refer to Patent Literature 1).

The above-described discrimination device that determines the appearance quality grades of grains is adapted to capture images of grains to be subjected to quality grade discrimination, the images being captured using the image-capturing unit, and thereby obtain the imaging data; obtain quality grade information on the grains (outer shape, area, length, width, color (RGB information), cracks in a body, etc.) on the basis of the imaging data; compare the quality grade information on the grains with a quality grade discrimination criteria that is specified in advance; and thus determine the quality grades of the grains.

In addition, the above-described discrimination device that determines appearance quality grades of grains is capable of readily and quickly determining the quality grades of numerous grains.

Meanwhile, according to traditional discrimination devices that determine appearance quality grades of grains, quality grade discrimination criteria are created by obtaining imaging data of multiple sample grains in advance; specifying quality grades of the respective sample grains sequentially while an operator visually confirms the imaging data on a display unit; and using quality grade information on the respective sample grains obtained on the basis of the imaging data.

However, since it requires proficiency to specify the quality grades as described above by the operator confirming the imaging data on the display unit, it is not easy to create quality grade discrimination criteria for granular materials in a discrimination device that determines appearance quality grades of grains.

Patent Literature 1 Japanese Patent Laid-Open No. 2011-242284

SUMMARY OF INVENTION

Technical Problem

In view of the above, an object of the present invention is to provide a method of creating quality grade discrimination criteria in a discrimination device that determines appearance quality grades of granular materials which enables an operator who is not a skilled operator to readily create the quality grade discrimination criteria for the granular materials.

Solution to Problem

In order to attain the above object, the present invention is a method of creating quality grade discrimination criteria in a discrimination device that determines appearance quality grades of granular materials, the discrimination device being adapted to capture images of granular materials by an image-capturing unit and thereby obtain imaging data, and determine quality grades of the granular materials on the basis of the imaging data, the method comprising: a granular material placement step of sorting the granular materials on a per-quality-grade basis and placing the granular materials on an image-capture surface of the image-capturing unit; an imaging data acquisition step of capturing images of the granular materials placed on the image-capture surface by the image-capturing unit and thereby obtaining the imaging data; a quality grade information acquisition step of obtaining, on a per-quality-grade basis, pieces of quality grade information on the respective granular materials on the basis of the imaging data; and a quality grade discrimination criteria creation step of creating quality grade discrimination criteria using the quality grade information obtained on a per-quality-grade basis.

The method of creating quality grade discrimination criteria in the discrimination device that determines appearance quality grades of granular materials may further include a quality grade name registration step of registering names of the quality grades of the granular materials.

In the method of creating quality grade discrimination criteria in the discrimination device that determines appearance quality grades of granular materials, the quality grade information obtained in the quality grade information acquisition step may include at least any one of: an outer shape; an area; a length; a width; a color; and cracks in a body, of the granular materials.

In the granular material placement step, the granular materials placed on the image-capture surface of the image-capturing unit may be accommodated in a tray divided into a plurality of regions and sorted on a per-quality-grade basis.

In the quality grade discrimination criteria creation step, the quality grade discrimination criteria may be created using a machine learning algorithm.

Advantageous Effects of Invention

The method of creating the quality grade discrimination criteria in the discrimination device that determines appearance quality grades of granular materials according to the present invention includes the granular material placement step where granular materials are sorted on a per-quality-grade basis and placed upon the image-capture surface of the image-capturing unit, and is capable of handling granular materials that are sorted in advance on a per-quality-grade basis, so that an operator who is not a skilled operator is allowed to readily create the quality grade discrimination criteria for the granular materials.

Also, since the operator places the granular materials sorted in advance on a per-quality-grade basis upon the image-capture surface of the image-capturing unit, it is made possible for a computer to automatically create the quality grade discrimination criteria.

Further, since the granular materials sorted in advance on a per-quality-grade basis can be used repeatedly, it is made possible to repeatedly create quality grade discrimination criteria having objectivity.

When the quality grade discrimination criteria creation step includes creating the quality grade discrimination criteria using a machine learning algorithm, it is made possible to readily create highly accurate quality grade discrimination criteria.

DESCRIPTION OF EMBODIMENTS

Embodiments of the present invention are described with reference to the drawings.
(Configuration of Discrimination Device that Determines Appearance Quality Grades of Granular Materials)

Figure 1:
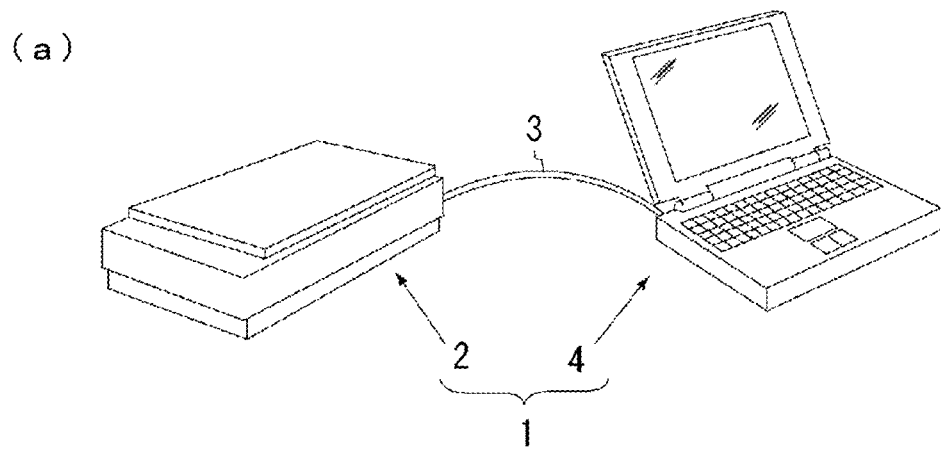
FIG. 1 is an explanatory diagram illustrating an example of a discrimination device that determines appearance quality grades of granular materials, the discrimination device being used in conjunction with a method in accordance with the present invention.
Figure 1:
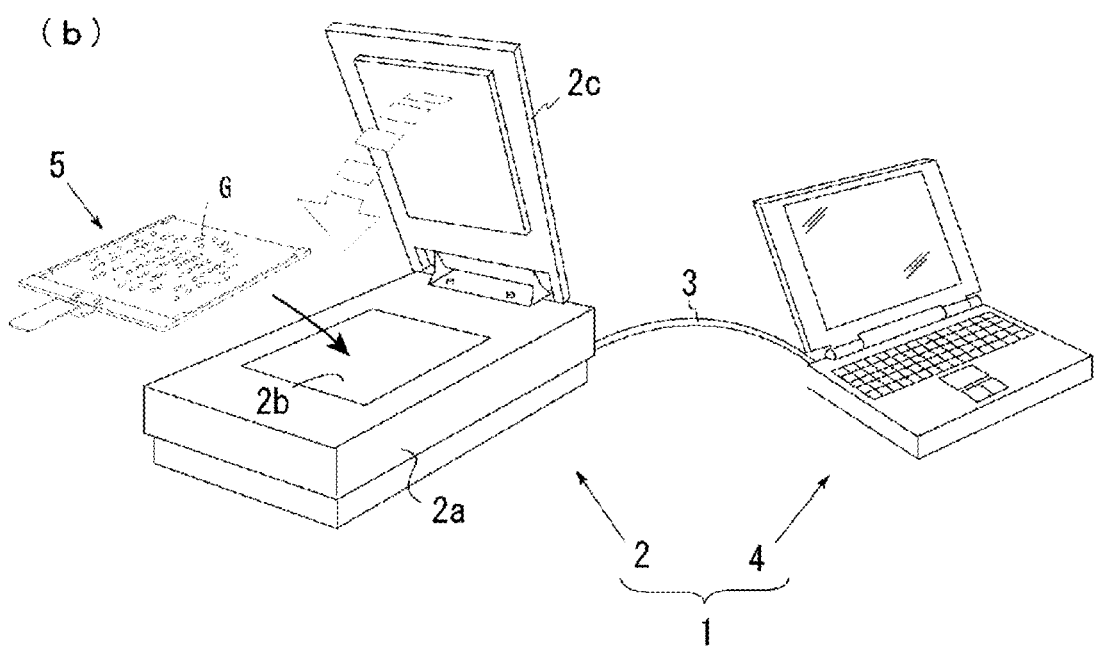

FIG. 1 illustrates an example of a discrimination device that determines appearance quality grades of granular materials, which is used in one embodiment of the present invention.

The discrimination device 1 that determines appearance quality grades of granular materials includes an image-capturing unit 2 configured to capture images of granular materials which may be grains such as rice, wheat, beans, and corns or pellets, and a computer 4 connected to the image-capturing unit 2 via a cable 3. By way of example, commercially available scanners and multifunctional devices may be used as the image-capturing unit 2.

The image-capturing unit 2 includes a body 2a, an image-capture surface 2b provided on an upper surface of the body 2a, and a cover 2c adapted to open and close the image-capture surface 2b. Also, the body 2a includes a light source including a white fluorescent light, a white LED, etc. that emits light toward the granular materials placed on the image-capture surface 2b, and a light receiving section including a color CCD line sensor, etc. that receives reflected light from the granular materials. Also, the granular materials G are accommodated by a tray 5 to rest thereon and thus placed on the image-capture surface 2b.

The computer 4 includes an image processing unit configured to carry out image processing on the imaging data of the granular materials captured by the image-capturing unit 2 and extract various pieces of quality grade information such as optical information including colors of the granular materials and shape information including outer shapes thereof; a quality grade discrimination criteria creation unit configured to create quality grade discrimination criteria using the quality grade information extracted by the image processing unit; a quality grade discrimination criteria storage unit configured to store the created quality grade discrimination criteria; a quality grade discrimination unit configured to determine the quality grades of the granular materials by using the quality grade discrimination criteria stored in the quality grade discrimination criteria storage unit; and a display unit configured to display a result obtained by the quality grade discrimination unit.

The above-described discrimination device 1 that determines appearance quality grades of granular materials transmits an imaging signal of the granular materials obtained by the image-capturing unit 2 to the computer 4, and the computer 4 determines the quality grades of the respective granular materials.

In the following, a method of creating the quality grade discrimination criteria in the discrimination device that determines appearance quality grades of granular materials is described.

(Procedure of Creation of Quality Grade Discrimination Criteria)

Figure 2:
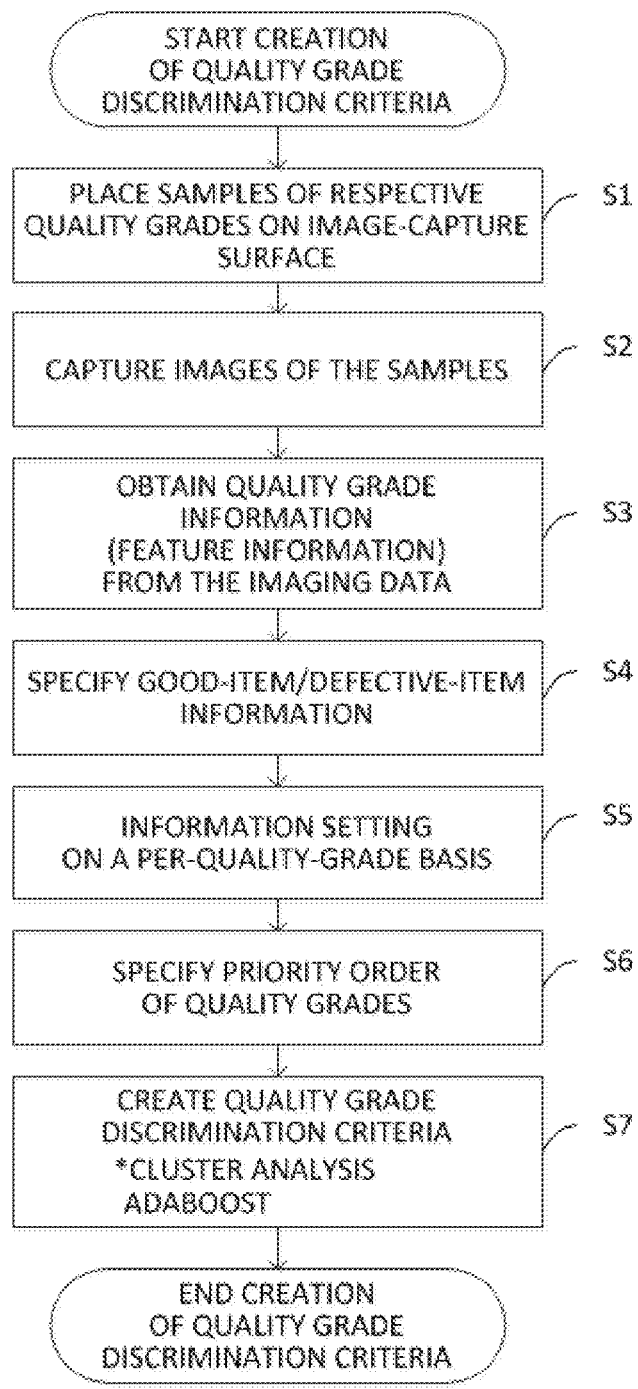
FIG. 2 is a flow diagram of a procedure of creating quality grade discrimination criteria.

FIG. 2 illustrates a flow of a procedure of creating the quality grade discrimination criteria in the discrimination device that determines appearance quality grades of granular materials.

(1) Step S1:

The image-capturing unit 2 illustrated in FIG. 1 can be used in the image capturing. An operator prepares in advance sample grains of the individual quality grades to be subjected to sorting, where, for example, in the case of rice grains, sample grains may include a whole grain, an immature grain, a broken grain, a cracked grain, a colored grain, a foreign particle, and the like, and the operator divides the sample grains into groups (A, B, C, . . . ), sorts these sample grains on a per-group basis and places them on the image-capture surface 2b of the image-capturing unit 2. Here, the number of the sample grains of the respective groups may be one, but larger numbers are desirable in order to obtain much quality grade information as described later. It should be noted that the numbers of grains do not need to be the same among the groups.

Figure 3:
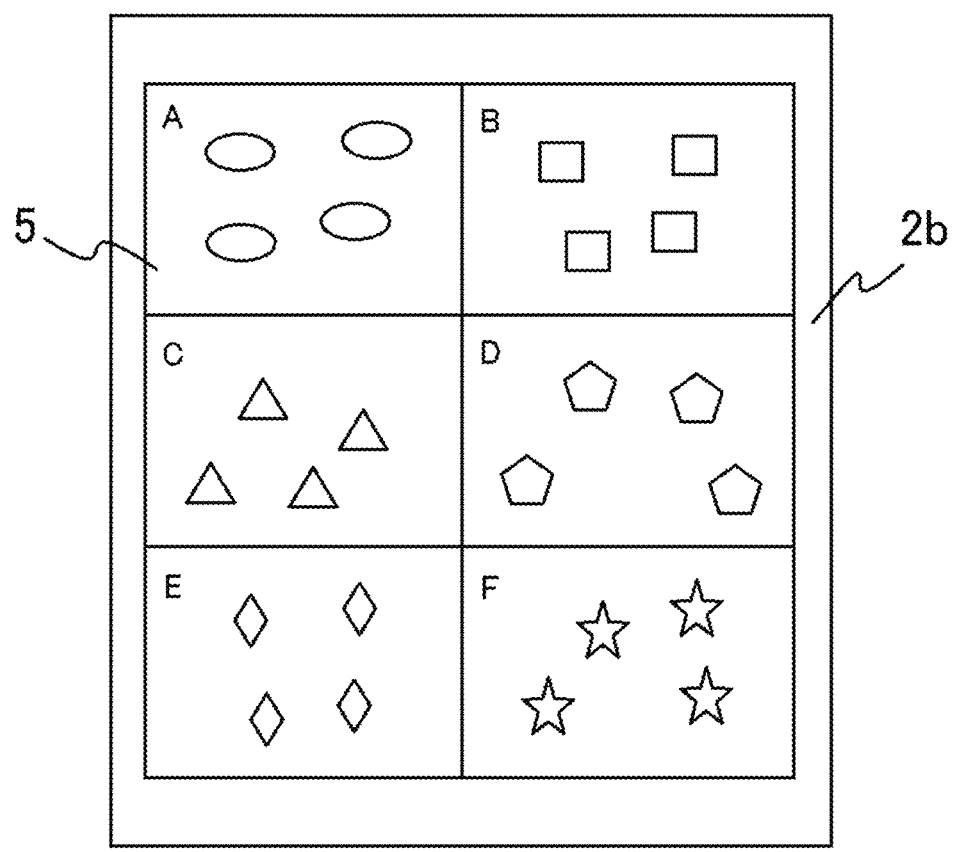
FIG. 3 is an explanatory diagram illustrating a state where granular materials are placed on an image-capture surface of an image-capturing unit.

As illustrated in FIG. 3, when the sample grains are placed upon the image-capture surface 2b of the image-capturing unit 2, the sample grains can be sorted on a per-group basis into the groups (A, B, C, . . . ) by accommodating them on the single tray 5 which is divided into multiple regions. Also, one tray may be provided for one group and thus the trays of the respective groups may be respectively placed on the image-capture surface 2b, or, in a case where it may not be possible to provide a tray, regions in which the respective groups are placed on a per-group basis may be provided on the image-capture surface 2 and the sample grains may be directly placed on the image-capture surface 2b such that the sample grain or grains of one group are not mixed with the sample grains of the other groups.

It should be noted that the sample grains need to be sorted on a per-group basis but do not need to be placed in the form of an array thereof.

(2) Step S2:

Image capturing is carried out for the sample grains sorted on a per-group basis and placed on the image-capture surface 2b of the image-capturing unit 2 in step S1, and pieces of imaging data of the respective sample grains are obtained.

(3) Step S3:

The computer 4 obtains pieces of quality grade information (feature information) on the respective sample grains on a per-group basis on the basis of the pieces of imaging data obtained in step S2.

Here, the quality grade information includes the outer shape, area, length, width, color (RGB information), cracking in a body, etc., of the sample grains.

(4) Step S4:

The operator specifies the individual groups as either a good item or a defective item while confirming the imaging data obtained in step S2 on the display unit (good item/defective item information specification).

Here, the above-described good item/defective item information specification is not indispensable in this embodiment. When the above-described good item/defective item information specification is carried out, it is made possible, in the quality grade discrimination of the granular material which is described later, to carry out classification on a per-good-item/defective-item basis in addition to discrimination on a per-quality-grade-name basis registered in the computer 4 in step S5 for the granular materials to be subjected to the quality grade discrimination.

(5) Step S5:

The operator registers (enters) names of the respective groups (quality grade names) in the computer 4 (quality grade name setting). As a result, the quality grade names are associated with the quality grade information and the good item/defective item information (quality grade-categorized information setting). It is assumed here that the sample grains to be subjected to the quality grade discrimination are rice grains and six types of quality grades are specified, i.e., whole grain, immature grain, broken grain, cracked grain, colored grain, and foreign particle.

(6) Step S6:

In a case where it is determined that any granular material falls under two or more quality grades in the quality grade discrimination of the granular materials which is described later, a priority order is specified in order to ensure that one granular material falls under only one quality grade (prioritized discrimination order setting). Meanwhile, it is also possible that a granular material is determined as falling under all the relevant quality grades without specifying the priority order. When the prioritized discrimination order setting is carried out, one sample grain will be counted as having one quality grade. When the prioritized discrimination order setting is not carried out, then one sample will be counted as falling under all the relevant quality grades.

(7) Step S7:

Quality grade discrimination criteria are created by using the above-described pieces of the quality grade information on the respective quality grades. In accordance with this embodiment, the computer 4 automatically creates the quality grade discrimination criteria by using analyses by cluster analysis and AdaBoost (machine learning algorithm). With regard to the cluster analysis, for example, refer to Japanese Patent Laid-Open No 2010-60389, etc. With regard to the AdaBoost analysis, for example, refer to Japanese Patent Laid-Open No. 2013-33331, etc.

<Example of Creation of Quality Discrimination Criteria>

An example of how the quality grade discrimination criteria are created is described.

Figure 4:
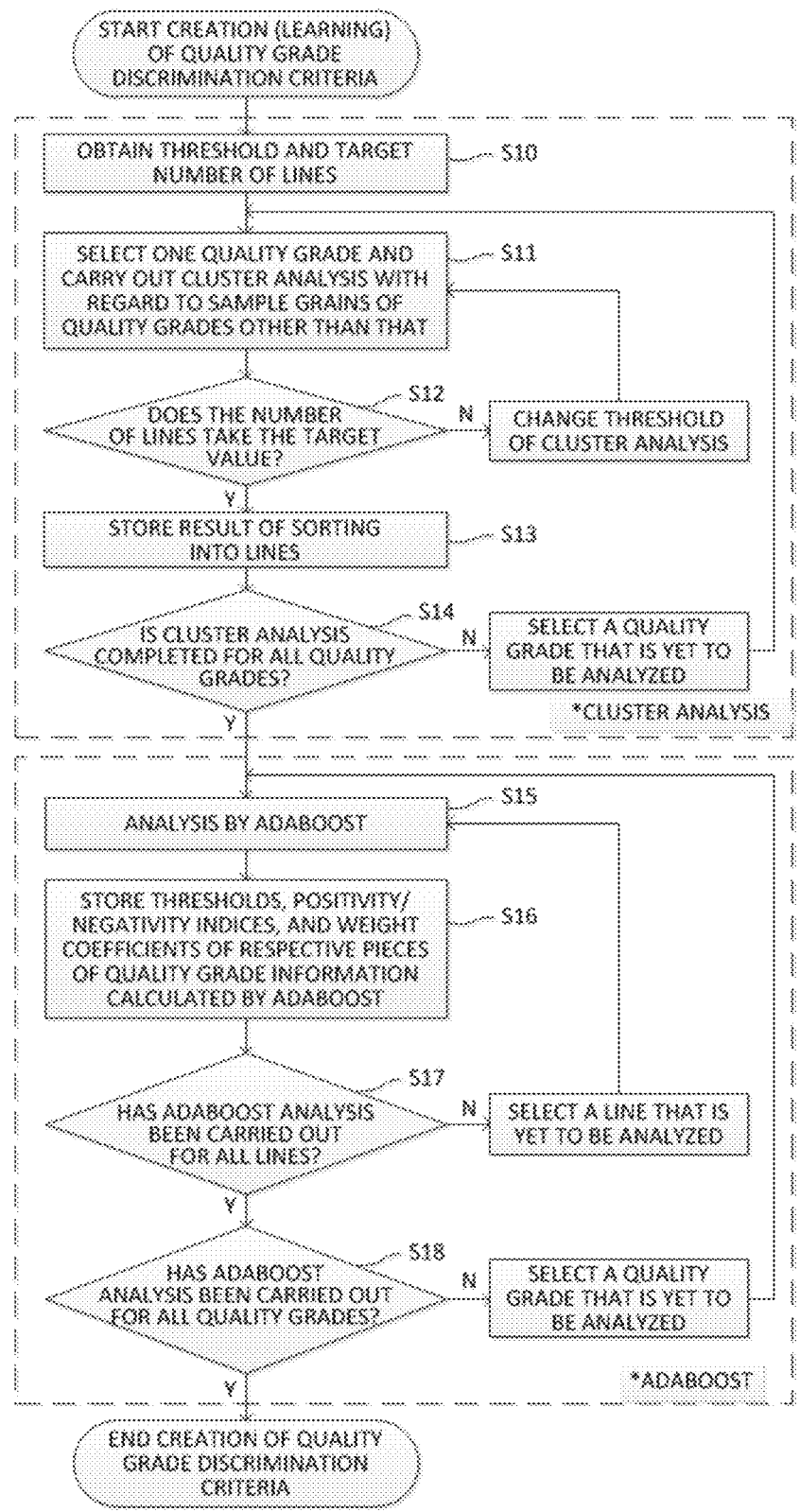
FIG. 4 is a flow diagram of an example of how the quality grade discrimination criteria are created.

FIG. 4 illustrates a flow of creation of the quality grade discrimination criteria using the analyses based on the cluster analysis and AdaBoost, which is an example of the quality grade discrimination criteria creation in step S7.

(a) Cluster Analysis (1) Step S10:

Thresholds used in this analysis and the target number of lines are obtained to carry out the cluster analysis. The threshold and the target number of lines are stored in advance in a memory unit of the computer 4. The thresholds are for use in classifying and sorting the respective sample grains into lines in the cluster analysis, and used to determine whether or not the distance between the lines calculated from the entered quality grade information is correct. The target number of lines is a target value of the number of the lines according to which classification and sorting is carried out by the cluster analysis.

(2) Step S11:

One quality grade is selected from the quality grade names registered in step S5, and the cluster analysis is carried out by using the quality grade information obtained in step S3 with regard to the sample grains of the remaining quality grades other than the selected one, i.e., the unselected quality grades. This analysis is preprocessing for carrying out the AdaBoost-based analysis, and the purpose of this preprocessing is to carry out classification and sorting for the sample grains of the above-described unselected quality grades independently of the quality grade name setting by the operator in step S5. By virtue of the classification and sorting by the cluster analysis, it is made possible to eliminate the impact of erroneous sorting or the like that occurs when the operator prepares in advance the sample grains of the respective quality grades in step S1.

(3) Step S12:

It is confirmed whether or not the sample grains have been classified and sorted to fall under the lines corresponding to the target number as a result of the classification and sorting by the cluster analysis in step S11. In this embodiment, the target number of lines is defined as six. This is the number of lines experimentally obtained as the one exhibiting good discrimination results.

As a result of the classification and sorting by the cluster analysis in step S11, when the number of lines is different from the target number of lines, then the threshold is modified and the cluster analysis is repeatedly carried out until the number of lines agrees with the above-described target number of lines. With regard to the threshold, since the number of lines is increased or decreased depending on the magnitude of the threshold, the threshold is automatically modified and the analysis is repeatedly carried out until sorting into the target number of lines is realized.

(4) Step S13:

Results of classification and sorting of the sample grains of the unselected quality grades into the target number of lines are stored. For example, if the quality grade selected in step S11 is the whole grain, then the sample grains other than that of the whole grain are classified and sorted into the six lines regardless of the quality grades registered by the operator in step S5. In step S13, these lines will be stored in accordance with the respective quality grades.

(5) Step S14:

The cluster analysis in step S11 is carried out for all the quality grades. In this embodiment, since classification is carried out based on the six quality grades in step S5, the cluster analysis is carried out for all of these quality grades on a per-quality-grade basis, and the lines are obtained on a per-quality-grade basis.

(b) AdaBoost-Based Analysis (6) Step S15:

In step S15, one of the quality grades registered in step S5 is selected, and the AdaBoost-based analysis is carried out by using the quality grade information obtained in step 3 with regard to the sample grains of the selected quality grade and the sample grains classified and sorted into one line among the lines in this quality grade (six lines in this embodiment), and the thresholds, positivity/negativity indices, and weight coefficients of the respective pieces of the quality grade information are calculated. In this embodiment, the threshold, the positivity/negativity indices, and the weight coefficient of the respective piece of the quality grade information become the quality grade discrimination criterion.

(7) Step S16:

In step S16, the analysis results such as the thresholds, the positivity/negativity indices, and the weight coefficients for the respective pieces of the quality grade information calculated by the analysis in step S15 are stored.

(8) Step S17:

With regard to the sample grains of the quality grade selected in step S15, it is confirmed whether or not the AdaBoost-based analysis has been carried out for all the lines. The AdaBoost-based analysis is carried out for each line.

(9) Step S18:

In step S18, it is confirmed whether or not the AdaBoost-based analysis has been carried out for all the quality grades. Creation of the quality grade discrimination criteria is completed, i.e., the learning is completed, when the AdaBoost-based analysis has been carried out for all the quality grades on a per-quality-grade basis; the thresholds, the positivity/negativity indices, and the weight coefficients of the respective pieces of the quality grade information have been calculated for all the lines under all the quality grades; and they have been stored as the quality grade discrimination criteria.

(Quality Grade Discrimination Procedure)

Figure 5:
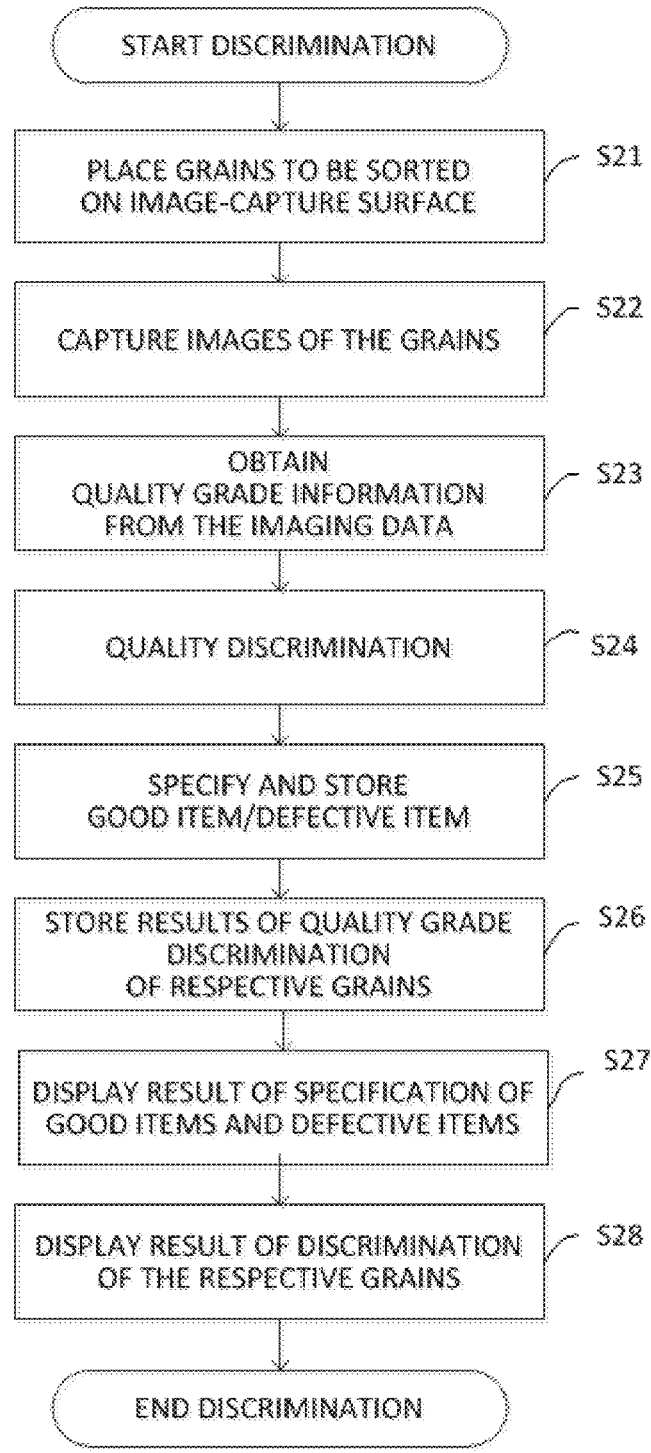
FIG. 5 is a flow diagram of a quality grade discrimination procedure.

FIG. 5 illustrates a flow of the quality grade discrimination procedure to determine the quality grades of the granular materials in the discrimination device that determines appearance quality grades of granular materials.

(1) Step S21:

Granular materials to be subjected to the quality grade discrimination are placed on the image-capture surface 2b of the image-capturing unit 2.

(2) Step S22:

Images of the granular materials placed on the image-capture surface 2b of the image-capturing unit 2 in step S21 are captured, and the imaging data for each granular material is obtained.

(3) Step S23:

The computer 4 obtains pieces of the quality grade information on the respective granular materials on the basis of the imaging data obtained in step S22. The quality grade information is the same information as that in step S3.

(4) Step S24:

The quality grades of the respective granular materials are determined by the AdaBoost-based analysis by using the quality grade information obtained in step S23 and the quality grade discrimination criteria created in advance.

(5) Step S25:

The computer 4 classifies the respective granular materials as either a good item or a defective item on the basis of the discrimination result in step S24 and the good item/defective item information in step S4 and stores the data.

(6) Step S26:

The quality grade discrimination results in step S24 are stored.

(7) Step S27:

The respective granular materials classified as a good item or a defective item are displayed as appropriate by the display unit on the basis of the sorting result in step S25.

(8) Step S28:

The determined respective granular materials are displayed as appropriate by the display unit on a per-quality-grade basis on the basis of the quality grade discrimination results in step S24.

<Example of Quality Grade Discrimination>

Figure 6:
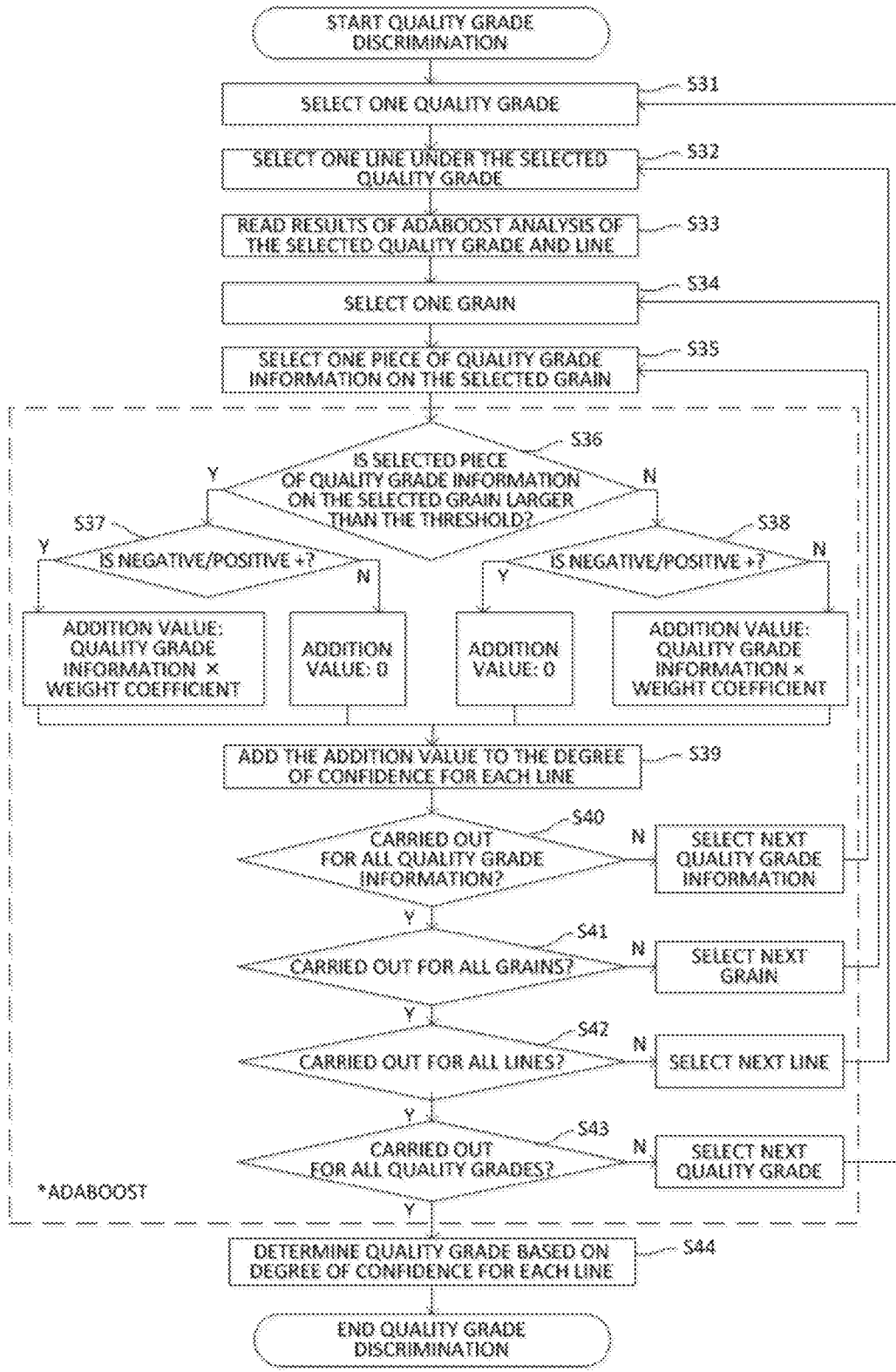
FIG. 6 is a flow diagram of an example of how the quality grades are determined.

FIG. 6 illustrates a quality grade discrimination flow, which is an example of the quality grade discrimination based on the quality grade discrimination criteria in step 24.

(1) Step S31:

First, one quality grade is selected in step S31.

(2) Step S32:

Since the lines in the number corresponding to the target value (six lines in this embodiment) are obtained for the selected quality grade by the cluster analysis, one line is selected therefrom.

(3) Step S33:

The analysis results by the AdaBoost of the selected quality grade and line, such as the threshold, the positivity/negativity index, and the weight coefficient of the respective piece of quality grade information which are stored in step S16, are read from the memory unit.

(4) Step S34:

One granular material is selected from the imaging data obtained by the image capturing.

(5) Step S35:

One piece of quality grade information regarding the selected granular material is selected.

The following is the AdaBoost-based analysis.

(6) Step S36:

With regard to the granular material selected in step S34, it is determined whether or not the quality grade information selected in step S35 is larger than the threshold read in step S33.

(7) Steps S37 and S38:

When the above-described quality grade information is larger than the above-described threshold, negativity or positivity is confirmed in step S37. In contrast, when the above-described quality grade information is smaller than the above-described threshold, then the negativity or positivity is confirmed in step S38. An addition value is obtained based on a result of the above-described confirmation of negativity or positivity.

Here, the "negativity or positivity" in accordance with this embodiment is a criteria (a flag) for determining, assuming a case where the above-described quality grade information resides on the plus side of the above-described threshold and another case where it resides on the minus side of it, whether a granular material is regarded as having the selected quality grade because the information resides on the plus side or on the minus side.

(8) Step S39:

In step S39, the addition value obtained in step S37 or S38 is added to a degree of confidence (or degree of similarity) obtained for each line.

(9) Step S40:

It is confirmed whether or not the operations of the steps S36 to S39 have been carried out for all pieces of the quality grade information. The discrimination in step S36 is carried out for all pieces of the quality grade information that are to be used.

(10) Step S41:

It is confirmed whether or not the operations of the steps S36 to S39 have been carried out for all the granular materials. The discrimination in step S36 is carried out for all the granular materials whose images have been captured.

(11) Step S42:

It is confirmed whether or not the operations of the steps S36 to S39 have been carried out for all the lines. The discrimination in step S36 is carried out for all the lines of the selected quality grade.

(12) Step S43:

It is confirmed whether or not the operations of the steps S36 to S39 have been carried out for all the quality grades. The discrimination in step S36 is carried out for all the quality grades specified in step S5.

(13) Step S44:

Multiple degrees of confidence are obtained for the respective granular materials whose images have been captured. The quality grades of the respective granular materials are determined on the basis of the magnitude of the degrees of confidence, etc. Thus, the discrimination of the quality grades is completed.

In accordance with the embodiment of the present invention, since sample grains are divided into groups (on a per-quality-grade basis) and placed on the image-capture surface 2b of the image-capturing unit 2, it is made possible to handle sample grains that are divided into groups in advance, so that an operator who is not a skilled operator is allowed to readily create the quality grade discrimination criteria for the granular materials.

Also, in accordance with the embodiment of the present invention, since the operator sorts and places the sample grains divided into groups in advance on the image-capture surface 2b of the image-capturing unit 2 on a per-group basis, it is made possible for the computer 4 to automatically create the quality grade discrimination criteria.

Further, in accordance with the method of creating the quality grade discrimination criteria according to the embodiment of the present invention, since the granular materials that were sorted in advance into respective groups can be repeatedly used, it is made possible to repeatedly create quality grade discrimination criteria having objectivity.

Since the embodiment of the present invention creates the quality grade discrimination criteria by using the cluster analysis and the AdaBoost-based analysis, it is made possible to create highly accurate quality grade discrimination criteria.

Although the cluster analysis and the AdaBoost-based analysis are used in creating the quality grade discrimination criteria in the embodiment of the above-described present invention, the quality grade discrimination criteria can also be created by using analyses based on other machine learning algorithms or other known methods.

It will be appreciated that the present invention is not limited to the above-described embodiment and that the configuration of the present invention can be modified as appropriate without departing from the scope of the invention.

INDUSTRIAL APPLICABILITY

The present invention is of considerable utility because it allows an operator who is not a skilled operator to readily create the granular material quality grade discrimination criteria.

REFERENCE SIGNS LIST

1 Discrimination device that determines appearance quality grades of granular materials 2 Image-capturing unit (scanner)
2a Body
2b Image-capture surface
2c Cover
3 Cable
4 Computer
5 Tray

The invention claimed is:

1. A method of creating quality grade discrimination criteria in a discrimination device that determines appearance quality grades of granular materials, the discrimination device being adapted to capture images of granular materials, sorted in advance on a per-quality basis, by an image-capturing unit and thereby obtain imaging data, and determine quality grades of the granular materials on the basis of the imaging data, the method comprising:

a granular material placement step of sorting the granular materials into a tray on a per-quality-grade basis and placing the granular materials on an image-capture surface of the image-capturing unit;

an imaging data acquisition step of capturing images of the granular materials placed on the image-capture surface by the image-capturing unit and thereby obtaining the imaging data;

a quality grade information acquisition step of obtaining, on a per-quality-grade basis, pieces of quality grade information on the respective granular materials on the basis of the imaging data; and a quality grade discrimination criteria creation step of creating quality grade discrimination criteria by using the quality grade information obtained on a per-quality-grade basis, wherein the number of granular materials sorted on a per-quality-grade basis is equal to or greater than one, wherein the quality grade information obtained in the quality grade information acquisition step includes at least any one of: an outer shape; an area; a length; a width; a color; and cracks in a body, of the granular materials, wherein, in the granular material placement step, the granular materials placed on the image-capture surface of the image-capturing unit are accommodated in a tray divided into a plurality of regions and sorted on a per-quality-grade basis, wherein, in the quality grade discrimination criteria creation step, the quality grade discrimination criteria are created using a machine learning algorithm.

2. The method of creating quality grade discrimination criteria according to claim 1, further comprising a quality grade name registration step of registering names of the quality grades of the granular materials.

3. The method of creating quality grade discrimination criteria of claim 1, wherein the machine-learning algorithm is Adaptive Boosting.

4. A method of creating quality grade discrimination criteria in a discrimination device that determines appearance quality grades of granular materials, the discrimination device being adapted to capture images of granular materials, sorted in advance on a per-quality basis, by an image-capturing unit and thereby obtain imaging data, and determine quality grades of the granular materials on the basis of the imaging data, the method comprising:

placing sample grains of individual quality grades into a tray, sorted into individual quality grade groups and placed directly or indirectly on an image-capture surface of the image-capturing unit;

capturing images of the sample grains with the image-capturing unit to obtain image data of the sample grains;

extracting pieces of quality grade information from the image data of the sample grains using a computer connected to the discrimination device; and classifying and sorting the sample grains by cluster analysis for all quality grades, using thresholds and target numbers of lines pre-stored in a memory unit of the computer and the extracted quality grade information;

creating quality grade discrimination criteria by calculating, on a per-quality-grade basis, thresholds, positivity/negativity indices, and weight coefficients of respective pieces of the quality grade information using a machine-learning meta-algorithm; and storing the quality grade discrimination criteria in the memory unit of the computer.

5. The method of creating quality grade discrimination criteria of claim 4, wherein the quality grade information includes at least one of: an outer shape; an area; a length; a width; a color; and cracks in a body, of the granular materials.

6. The method of creating quality grade discrimination criteria of claim 4, wherein the machine-learning meta-algorithm is Adaptive Boosting.

* * * * *